United States Patent
Takizawa et al.

(10) Patent No.: US 8,197,859 B2
(45) Date of Patent: Jun. 12, 2012

(54) LIPOLYSIS STIMULATOR

(75) Inventors: Minoru Takizawa, Tochigi (JP); Mayumi Sato, Tochigi (JP); Hiroshi Kusuoku, Tochigi (JP); Mitsuyoshi Sakasai, Tochigi (JP)

(73) Assignee: Kao Corporation, Tokyo (JP)

( * ) Notice: Subject to any disclaimer, the term of this patent is extended or adjusted under 35 U.S.C. 154(b) by 171 days.

(21) Appl. No.: 12/296,213

(22) PCT Filed: Mar. 13, 2007

(86) PCT No.: PCT/JP2007/000216
§ 371 (c)(1),
(2), (4) Date: Dec. 30, 2008

(87) PCT Pub. No.: WO2007/116579
PCT Pub. Date: Oct. 18, 2007

(65) Prior Publication Data
US 2010/0285153 A1    Nov. 11, 2010

(30) Foreign Application Priority Data
Apr. 7, 2006    (JP) ................................ 2006-106092

(51) Int. Cl.
*A61K 36/00*    (2006.01)
(52) U.S. Cl. ...................................................... 424/725
(58) Field of Classification Search .................. None
See application file for complete search history.

(56) References Cited

U.S. PATENT DOCUMENTS

| | | | |
|---|---|---|---|
| 4,288,433 A | 9/1981 | Koulbanis et al. | |
| 5,698,199 A | 12/1997 | Mori et al. | |
| 6,953,583 B1 * | 10/2005 | Ghisalberti | 424/401 |
| 7,300,675 B2 * | 11/2007 | Mori et al. | 424/724 |
| 2004/0208902 A1 | 10/2004 | Gupta | |
| 2005/0064049 A1 | 3/2005 | Mori et al. | |
| 2008/0021418 A1 | 1/2008 | Mori et al. | |

FOREIGN PATENT DOCUMENTS

| | | |
|---|---|---|
| EP | 1 502 598 A2 | 2/2005 |
| JP | 53-59038 | 5/1978 |
| JP | 08-26962 | 1/1996 |
| JP | 08-081382 A | 3/1996 |
| JP | 08-245410 A | 9/1996 |
| JP | 08-301780 A | 11/1996 |
| JP | 2004-75638 A | 3/2004 |
| JP | 2005-60366 | 3/2005 |
| JP | 2005-64049 A | 3/2005 |

OTHER PUBLICATIONS

Ateya, A-M., "Determination of Saponin Content in Certain Egyptian Plants by the Blood-Agar Haemolytic Zone Method," *Zag. J. Pharm. Sci.* 1:60-67, University of Zagazig (1994).
Patent Abstracts of Japan, English language abstract of Japanese Patent JP 08-81382 A.
Patent Abstracts of Japan, English language abstract of Japanese Patent JP 08-245410 A.
Patent Abstracts of Japan, English language abstract of Japanese Patent JP 08-301780 A.
Patent Abstracts of Japan, English language abstract of Japanese Patent JP 2004-075638 A.
Patent Abstracts of Japan, English language abstract of Japanese Patent JP 2005-064049 A.
International Search Report for International Application No. PCT/JP2007/000216, mailed on May 29, 2007, Japanese Patent Office, Tokyo, Japan.
Patent Abstracts of Japan, English language abstract of Japanese Patent JP-A-08-026962.
Patent Abstracts of Japan, English language abstract of Japanese Patent JP 2005-60366.
Extended European Search Report for EP 07736875.1-1212 (supplementary European search report and the European search opinion), dated Nov. 27, 2009, European Patent Office, The Hague, The Netherlands.
International Preliminary report on Patentability, issued Oct. 8, 2008, that includes the original Japanese language Written Opinion for PCT/JP2007/000216, filed Mar. 13, 2007, The International Bureau of WIPO, Geneva, Switzerland.
International Preliminary report on Patentability issued Dec. 10, 2008, that includes the English language translation of the Written Opinion for PCT/JP2007/000216, filed Mar. 13, 2007, The International Bureau of WIPO, Geneva, Switzerland.

* cited by examiner

*Primary Examiner* — Qiuwen Mi
(74) *Attorney, Agent, or Firm* — Sterne Kessler Goldstein & Fox P.L.L.C.

(57) ABSTRACT

To provide a lipolysis agent, a slimming agent, and a cellulite-ameliorating agent, which stimulate decomposition of fat accumulated in the adipose tissue, to thereby exhibit body-slimming effect and which is effective for inhibition or prevention of obesity and amelioration of prone to obesity. The lipolysis stimulator of the invention contains, as effective ingredients, a plant Huang Hua Cai or an extract thereof, and a xanthine derivative.

7 Claims, 3 Drawing Sheets

LIPOLYSIS STIMULATOR

TECHNICAL FIELD

The present invention relates to a lipolysis stimulator and a slimming agent which are effective for inhibition or prevention of obesity, amelioration of prone to obesity and the like.

BACKGROUND OF THE INVENTION

Life styles in developed countries induce lack of physical exercise and excess of calories intake. As a result, people living in those countries tend to become obese. Obesity is caused by taking into the body an excessive of energy over the energy consumed by the body, and accumulation of the excessive energy as neutral fat in white adipocytes.

Obesity readily triggers diseases whose incidences are higher in developed countries, such as myocardial infarction, arteriosclerosis, and insulin resistance. Therefore, obesity is a serious problem in developed countries from the viewpoint of prevention of these diseases.

Meanwhile, neutral fat is readily accumulated as so-called subcutaneous fat, particularly in local sites such as the abdomen corresponding to the intestines, waist, buttocks, and thighs. Such fat accumulation results in a very unfavorable body shape. Furthermore, accumulation of water and waste matter in adipocytes leads to formation of cellulite, which makes the skin surface dimpled or uneven. Since cellulite imparts a cottage cheese-like texture to the skin, it is not preferred from the aesthetic viewpoint.

One known mechanism of stimulating lipolysis in the body includes activation of adenylate cyclase, and increase of cAMP (cyclic adenosine monophosphate) level in adipocytes by inhibiting PDE (phosphodiesterase) to prevent cAMP from degradation.

For example, through taking in a xanthine derivative that has a PDE inhibitory action; such as caffeine or theophylline, hormones acting on the sympathetic nerves such as noradrenalin and adrenalin are activated, whereby lipolysis is stimulated (see Patent Documents 1 and 2).

Moreover, plants containing caffeine; such as coffee beans, green tea, oolong tea, and mate tea, are known to have a lipolysis-stimulating action. Meanwhile, a plant Huang Hua Cai is known as a flower of *Hemerocallis plicata* Stepf, and has a diuretic action and an edema-ameliorating action. In addition to these actions, Huang Hua Cai has been recently reported to have a lipolysis-stimulating action (see Patent Document 3).

Patent Document 1: JP-A-53-059039
Patent Document 2: JP-A-08-026962
Patent Document 3: JP-A-2005-060366

SUMMARY OF THE INVENTION

The present invention provides the following inventions 1 to 10.
1. A lipolysis stimulator containing a plant Huang Hua Cai or an extract thereof, and a xanthine derivative, as effective ingredients.
2. A slimming agent containing a plant Huang Hua Cai or an extract thereof, and a xanthine derivative, as effective ingredients.
3. A cellulite-reducing agent containing a plant Huang Hua Cai or an extract thereof, and a xanthine derivative, as effective ingredients.
4. Use of a plant Huang Hua Cai or an extract thereof, and a xanthine derivative, as a lipolysis stimulator.
5. Use of a plant Huang Hua Cai or an extract thereof, and a xanthine derivative, as a slimming agent.
6. Use of a plant Huang Hua Cai or an extract thereof, and a xanthine derivative, as a cellulite-reducing agent.
7. A method of stimulating lipolysis, including causing a subject in need thereof to ingest a plant Huang Hua Cai or an extract thereof, and a xanthine derivative, or administering a plant Huang Hua Cai or an extract thereof, and a xanthine derivative to a subject in need thereof.
8. A method of reducing cellulite, including causing a subject in need thereof to ingest a plant Huang Hua Cai or an extract thereof, and a xanthine derivative, or administering a plant Huang Hua Cai or an extract thereof, and a xanthine derivative to a subject in need thereof.
9. A body-slimming method, including causing a subject in need thereof to ingest a plant Huang Hua Cai or an extract thereof, and a xanthine derivative, or administering a plant Huang Hua Cai or an extract thereof, and a xanthine derivative to a subject in need thereof.
10. A body-slimming method, including applying a plant Huang Hua Cai or an extract thereof, and a xanthine derivative, to the skin of a subject in need thereof.

Figure 1:
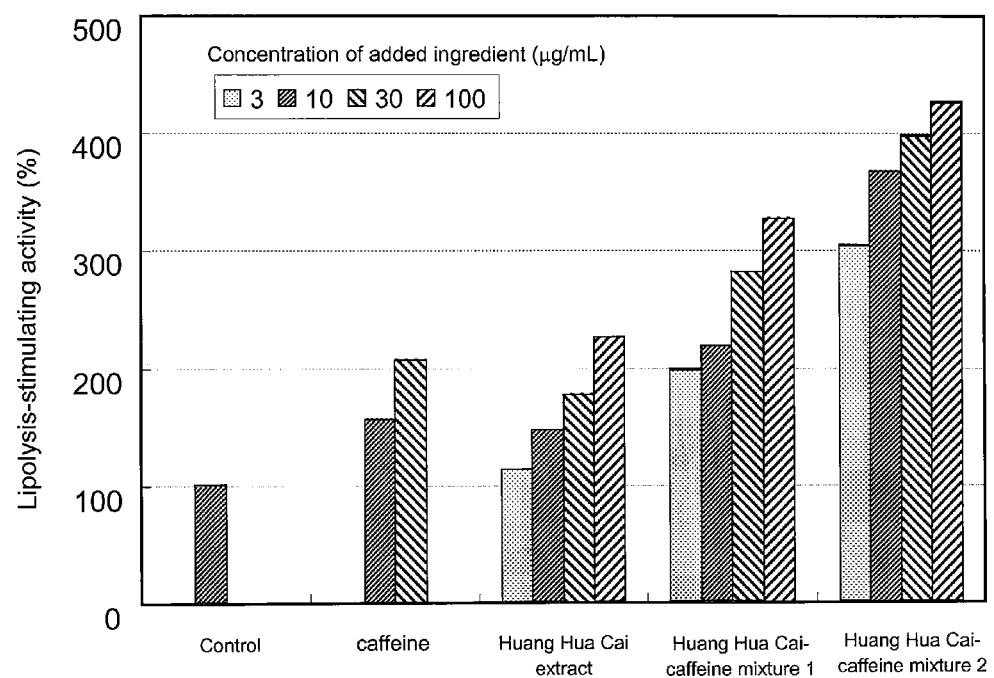
FIG. 1

A graph showing relative lipolysis-stimulating activities of caffeine, a Huang Hua Cai extract, a Huang Hua Cai-caffeine mixture 1, and a Huang Hua Cai-caffeine mixture 2, with respect to 100% activity of a control. The Huang Hua Cai-caffeine mixture 1 contains the Huang Hua Cai extract of each concentration and 10 μg/mL caffeine, and the Huang Hua Cai-caffeine mixture 2 contains the Huang Hua Cai extract of each concentration and 30 μg/mL caffeine.

FIG. 2

A graph showing relative lipolysis-stimulating activities of theophylline, a Huang Hua Cai extract, a Huang Hua Cai-theophylline mixture 1, and a Huang Hua Cai-theophylline mixture 2, with respect to 100% activity of a control. The Huang Hua Cai-theophylline mixture 1 contains the Huang Hua Cai extract of each concentration and 1 μg/mL theophylline, and the Huang Hua Cai-theophylline mixture 2 contains the Huang Hua Cai extract of each concentration and 3 μg/mL theophylline.

FIG. 3

A graph showing relative lipolysis-stimulating activities of aminophylline, a Huang Hua Cai extract, a Huang Hua Cai-aminophylline mixture 1, and a Huang Hua Cai-aminophylline mixture 2, with respect to 100% activity of a control. The Huang Hua Cai-aminophylline mixture 1 contains the Huang Hua Cai extract of each concentration and 1 μg/mL aminophylline, and the Huang Hua Cai-aminophylline mixture 2 contains the Huang Hua Cai extract of each concentration and 3 μg/mL aminophylline.

PREFERRED MODES FOR CARRYING OUT THE INVENTION

The present invention provides cosmetic products, quasi-drugs, drugs, or food products which can effectively stimulate decomposition of fat accumulated in the adipose tissues; for example, subcutaneous fat, whereby inhibition or prevention of obesity, amelioration of prone to obesity, reduction of cellulite, and the like can be effectively realized.

The present inventors have found that, when a plant Huang Hua Cai or an extract thereof and a xanthine derivative such as caffeine or theophylline are employed in combination, decomposition of neutral fat accumulated in adipocytes (adipose tissue) can be remarkably stimulated as compared with single use of respective components, whereby cosmetic products, quasi-drugs, drugs or food products containing both ingredients exhibit excellent effect on inhibition or prevention of obesity and on amelioration of prone to obesity.

Therefore, the lipolysis stimulator and a similar agent of the present invention can realize inhibition or prevention of obesity, amelioration of prone to obesity, reduction of cellulite and the like.

The "plant Huang Hua Cai" collectively refers to flowers and buds of Liliaceae plants of Shoyokanzo (*Hemerocallis plicata* Stepf) (Chinese medicine encyclopedia, published by the Shanghai Science Technology and Shogakukan Inc., Vol. 1, 1985, p. 114); Honkanzo (*Hemerocallis fulva* L.) (Chinese medicine encyclopedia, published by the Shanghai Science Technology and Shogakukan Inc., Vol. 1, 1985, p. 378); Yabukanzo (*Hemerocallis fulva* L.) (Chinese medicine encyclopedia, published by the Shanghai Science Technology and Shogakukan Inc., Vol. 1, 1985, pp. 381 & 539); Manshukisuge (*Hemerocallis flava* L.) (Chinese medicine encyclopedia, published by the Shanghai Science Technology and Shogakukan Inc., Vol. 1, 1985, pp. 378 & 539); Hosobakisuge (*Hemerocallis minor* Mill.) (Chinese medicine encyclopedia, published by the Shanghai Science Technology and Shogakukan Inc., Vol. 1, 1985, pp. 378 & 539); and allied plants thereof.

In the present invention, the "plant Huang Hua Cai" encompasses all the plants belonging to the aforementioned species. Buds of Huang Hua Cai available on the market themselves or a dried product thereof (also called Jin Zhen Cai) is used preferably. Note that drying of the plant can be performed through a generally employed plant drying method, and any of solar evaporation, air drying, heating, and freeze-drying may be employed.

The extract of the plant Huang Hua Cai employed in the present invention includes an extract of the plant Huang Hua Cai obtained through extraction with a solvent at ambient temperature or under heating, a diluted product thereof, a concentrate thereof, a dried product thereof and the like. Extraction may be performed through any of immersion, decoction, percolation, reflux extraction, supercritical extraction, ultrasonic extraction, microwave extraction and the like.

The extraction solvent to be used for obtaining the plant extract of the present invention may be either a polar or a non-polar solvent. A mixture of a polar and a non-polar solvent may also be employed.

The polar or non-polar solvents include water, alcohols, ketones, esters, chain or cyclic ethers, polyethers, hydrocarbons, aromatic hydrocarbons, pyridines, supercritical carbon dioxide, fats and oils, waxes, and other oils.

The alcohols include methanol, ethanol, propanol, butanol, propylene glycol, and butylene alcohol. The ketones include acetone and methyl ethyl ketone. The esters include methyl acetate and ethyl acetate. The chain or cyclic ethers include tetrahydrofuran and diethyl ether. The polyethers include polyethylene glycol. The hydrocarbons include hexane, cyclohexane, and petroleum ether. The aromatic hydrocarbons include benzene and toluene.

Among these solvents, water, alcohols, or a water-alcohol mixture is preferably used. A water-alcohol mixture is more preferred, with a water-methanol or water-ethanol mixture being even more preferred. When a water-alcohol mixture is employed, the mixing ratio (V/V) is preferably 0 to 80%, more preferably 0 to 60%.

The amount of solvent used in the present invention for extracting Huang Hua Cai, which varies depending on the type of the solvent, is preferably 1 to 100 parts by mass with respect to 1 part by mass of a Huang Hua Cai dried product, more preferably 5 to 20 parts by mass.

The extraction temperature is 5 to 70° C., preferably 5 to 50° C., more preferably 10 to 40° C., and the extraction time is one hour to 30 days, preferably 7 to 14 days.

The Huang Hua Cai extract as is or a diluted product may be used. Alternatively, the extract may also be used after being processed. Specifically, the extract may be concentrated (under reduced pressure, by freezing, or through a membrane) or dried (air-blowing, heating, or freezing), and may further be prepared into a paste or a dried product (powder).

Before use, the Huang Hua Cai extract is preferably purified through a known technique such as liquid-liquid partition, solid-liquid partition, membrane filtration, activated carbon technique, resin adsorption technique, or ion-exchange resin technique, to thereby removing inert contaminants. Optionally, the extract may be further subjected to a process such as deodorizing or decoloring before use.

In the present invention, the xanthine derivative refers to a compound belonging to the class of known compounds having a PDE inhibitory activity, a central excitatory action, a diuretic action and the like. Specific examples of the derivative include xanthine and a compound represented by the following formula (1):

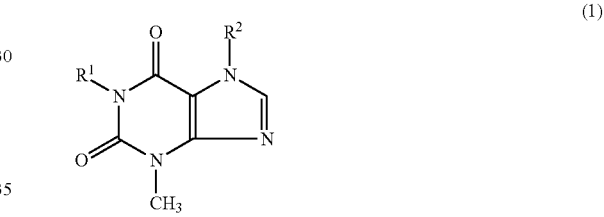

(1)

(wherein $R^1$ represents a methyl group or a hydrogen atom, $R^2$ represents a hydrogen atom or a C1 to C12 alkyl group (such as methyl, ethyl, propyl, butyl, or hexyl) which may have one or two substituents selected from a hydroxy group and a C1 to C10 alkanoyl group (such as formyl, acetyl, propanoyl, or butanoyl)), and salts thereof (such as salts of mineral acid such as hydrochloric acid or sulfuric acid, ethylenediamine salts, choline salts, and salts of organic acid such as acetic acid or citric acid).

In detail, the derivatives include xanthine, caffeine, theophylline, aminophylline, choline-theophylline (oxytriphylline), theobromine, diprophylline, and proxyphylline. Of these, aminophylline, theophylline, and caffeine are preferred. These xanthine derivatives may be used singly or in combination of two or more species.

The xanthine derivative employed in the present invention may be a commercial product. Alternatively, an extract from a plant containing the derivative and a xanthine derivative chemically synthesized through a known method may also be employed.

As described hereinbelow in the Examples section, the combination of the Huang Hua Cai or the extract thereof and the xanthine derivative according to the present invention synergistically potentiates the lipolysis activity of norepinephrine in rat abdominal subcutaneous adipose tissue. Therefore, through administration of such ingredients to a subject of interest, the body of the subject can be slimmed. Moreover, since the above activity is also exerted in the visceral adipose tissue, these ingredients can serve as a lipolysis stimulator, a slimming agent, and cellulite-reducing agent (hereinafter collectively referred to as "lipolysis stimulator and a similar agent"), each exerting body-slimming effects; such as inhibition or prevention of obesity and amelioration of prone to obesity and the like. The ingredients may also be used for producing the lipolysis stimulator and a similar agent. In other words, the lipolysis stimulator and a similar agent of the present invention stimulate lipolysis of neutral fat stored in adipose tissue, for example, subcutaneous fat, and further decomposition of cellulite, to thereby exhibit body-slimming effects; such as inhibition or prevention of obesity and amelioration of prone to obesity and the like. Therefore, the lipolysis stimulator and a similar agent can serve as a cosmetic product, a quasi-drug, a drug, a food product and the like, for body slimming purposes.

Moreover, the lipolysis stimulator and a similar agent of the present invention may be incorporated into food products which are produced based on the concept of imparting physiological functions to the body, such as inhibition or prevention of obesity and amelioration of prone to obesity, to thereby produce food products exhibiting lipolysis-stimulating effect and body-slimming effect, for example, to produce such products as bearing labels indicating that the food products are good for stimulating lipolysis, body-slimming, or cellulite reduction; such as functional food products, food products and beverages for the sick, and food products for specified health uses.

When the lipolysis stimulator or a similar agent of the present invention is ingested as food products, various food forms are conceivable, such as breads, cakes, noodles, sweets, jellies, chilled foods, ice cream, milk products, beverages, soup and the like, as well as tablets, capsules, syrups and the like.

The lipolysis stimulator and a similar agent of the present invention may be administered as a drug. The forms of the drug for oral administration include tablets, capsules, granules, powders, syrups and the like; and the forms of the drug for parenteral administrations include injections, suppositories, inhalations, percutaneously absorbable agents, external preparations and the like.

The lipolysis stimulator and a similar agent of the present invention may be used as quasi-drugs or cosmetic products, including skin external preparations, cleansing agents, bath agents, and make-up cosmetics and the like. The forms of the products may be selected from lotion, milky lotion, gel, cream, ointment, powder, granules and the like, depending on the application.

The aforementioned cosmetic products, quasi-drugs, drugs, food products and the like may be prepared through a routine preparation method. Specifically, the methods include mixing the raw materials with an optional carrier acceptable in drug preparation, dispersing the mixture, and forming into a shape of interest. If needed, one or more appropriate ingredients such as powders, oils or oily substances, antiseptic agents, antioxidants, moisturizing agents, buffers, surfactants, thickeners, activity-enhancers, colorants, perfumes, UV-absorbers, anti-inflammatory agents, bactericides, blood-circulation-enhancers, vitamins, and agents or medical properties of natural products having a lipolysis stimulating action or an uncoupling protein expression stimulating action, may be added to the products. These ingredients may be used in combination.

The powders include chalk, talc, Fuller's earth, kaolin, mica, starch, rubber, colloidal silica, sodium polyacrylate, cellulose powder, nylon powder, cross-linked silicone powder, cross-linked methylpolysiloxane, porous cellulose powder, porous nylon powder, anhydrous silica, zinc oxide, and titanium oxide. The oils or oily substances include fats and oils, waxes, hydrocarbons, higher fatty acids, higher alcohols, esters, essential oils, silicone oils, and fluorine-containing oils.

The fats and oils include natural ones such as soybean oil, rice oil, jojoba oil, avocado oil, almond oil, olive oil, cacao oil, sesame oil, persic oil, castor oil, coconut oil, mink oil, beef tallow and lard; and synthetic triglycerides such as hardened oils produced through hydrogenation of these natural fats and oils, myristic glyceride and 2-ethylhexanoic triglyceride. The waxes include carnauba wax, spermaceti wax, bees wax, and lanolin. The hydrocarbons include liquid paraffin, vaseline, paraffin microcrystalline wax, ceresin, squalane, and pristane. The higher fatty acids include lauric acid, myristic acid, palmitic acid, stearic acid, behenic acid, oleic acid, linoleic acid, linolenic acid, lanolic acid, and isostearic acid. The higher alcohols include lauryl alcohol, cetyl alcohol, stearyl alcohol, oleyl alcohol, lanolin alcohol, cholesterol, and 2-hexyldecanol. The esters include cetyl octanoate, triglyceride octanoate, myristyl lactate, cetyl lactate, isopropyl myristate, myristyl myristate, octyl dodecyl myristate, isopropyl palmitate, isopropyl adipate, butyl stearate, decyl oleate, cholesteryl isostearate, and POE sorbitol fatty acid esters. The essential oils include mint oil, jasmine oil, camphor oil, hinoki oil, tohi oil, pomegranate oil, turpentine oil, cinnamon oil, bergamot oil, mandarin oil, calamus oil, pine oil, lavender oil, bay oil, clove oil, hiba oil, rose oil, eucalyptus oil, lemon oil, thyme oil, peppermint oil, rose oil, sage oil, menthol, cineole, eugenol, citral, citronellal, borneol, linalool, geraniol, camphor, thymol, spilanthole, pinene, limonene, and terpene compounds. The silicone oils include dimethylpolysiloxane, dimethylcyclopolysiloxane, methylphenylpolysiloxane, methylhydrogen polysiloxane, and higher-alcohol-modified organopolysiloxane. The fluorine-containing oils include fluoro-polyether and perfluoroalkyl ether silicone.

The antioxidants include butylhydroxytoluene and ascorbic acid salts.

The moisturizing agents include glycerol, sorbitol, 2-pyrrolidon-5-carboxylate, dibutyl phthalate, gelatin, and polyethylene glycol.

The buffers include triethanolamine-lactate and sodium hydroxide-lactate.

In the present invention, any of anionic, cationic, nonionic, ampholytic, and silicone-based surfactants may be employed. The anionic surfactants include alkylbenzenesulfonate salts, alkyl or alkenyl sulfate salts, polyoxyethylene alkyl sulfate esters, alkyl ether or alkenyl ether sulfate salts, olefinsulfonate salts, alkanesulfonate salts, fatty acid alkali metal salts, unsaturated fatty acid salts, alkyl ether or alkenyl ether carboxylate salts, salts and esters of an α-sulfofatty acid having an alkyl group or an alkenyl group, N-acylamino acid-type surfactants having an acyl group and a free carboxylic acid residue, polyoxyethylene-hardened castor oil alkyl sulfate esters, polyoxyethylene alkyl phosphate esters, and phosphate monoester or diester surfactants having an alkyl group or an alkenyl group. The cationic surfactants include alkyltrimethylammonium salts, alkylpyridinium salts, quaternary alkylammonium salts, alkyldimethylbenzylammonium salts, alkylamine salts, polyamine fatty acid derivatives, amyl alcohol fatty acid derivatives, benzalkonium chloride, and benzethonium chloride. The nonionic surfactants include polyoxyethylene alkyl ethers, polyoxyethylene alkyl phenyl ethers, polyoxyethylene fatty acid esters, sorbitan fatty acid esters, polyoxyethylene sorbitan fatty acid esters, polyoxyethylene sorbitol fatty acid esters, fatty acid monoglycerides, polyoxyethylene-hardened castor oil, polyoxyethylene castor oil, polyglycerin fatty acid esters, sucrose fatty acid esters, glycerin fatty acid esters, and alkyl glyceryl ethers. The ampholytic surfactants include imidazoline-type ampholytic surfactants having an alkyl group, an alkenyl group, or an acyl group, and carbobetaine-type, amidobetaine-type, sulfobetaine-type, hydroxysulfobetaine-type, and amidosulfobetaine-type surfactants. The silicone surfactants include polyether-modified silicone and polyglycerin-modified silicone. The thickening agents include xanthan gum, hydroxyethyl cellulose, methylcellulose, and hydroxypropyl guar gum.

The coloring agents include the dyes in the Annexed Lists I and II of tar-based dyes prescribed under the Ministry of Health and Welfare Act of Japan, such as Yellow Color No. 4, Blue Color No. 1, and Yellow Color No. 202; and natural dyes approved as food additives, such as chlorophyll, riboflavin, crocin, safflower, and anthraquinone. The blood-circulation-enhancers include capsicins, calcium hopantenate, methyl nicotinate, tocopherol nicotinate, menthol, and camphor. The vitamins include fat-soluble vitamins such as vitamins A, $D_2$, $D_3$, E, and F; and water-soluble vitamins such as vitamin $B_1$, $B_2$, $B_6$, and $B_{12}$, folic acid, biotin, vitamin C, and vitamin P.

The effective ingredients of the drug, natural product or similar substances having a lipolysis stimulating action or an uncoupling protein expression stimulating action include β-adrenergic stimulants, α-adrenergic inhibitors, bipyridine derivatives, isoflavonic acid, rosisterol, octacosanol, hydroxytyrosol, grapefruit oil, raspberry ketone, zingerone, and extracts of plants such as thistle (*Cirsium*), family Piperaceae, family Rutaceae, family Menispermaceae, Kigelia plants, *Gynostemma pentaphyllum*, Atractylodis lanceae Rhizoma, benzoin, Coisis Semen, azuki bean, fennel, Tabebuia, Geranium herb, *Scutellaria baicalensis*, peach, thyme, chinese peony, tea leaves, *Cola acuminata*, *Swertia Japonica*, *Cinnamomi Cortex*, *Sanguisorba officinalis*, sage, rosemary, loquat, bladderwrack, carrot or ginseng, shiitake mashroom, *Saxifraga stolonifera*, and ginkgo.

The Huang Hua Cai (or the extract) content of the lipolysis stimulator or a similar agent according to the present invention is preferably 0.0001 to 30 mass % based on the dried state, more preferably 0.0002 to 5 mass %, and the xanthine derivative content is preferably 0.001 to 2 mass %, more preferably 0.005 to 1 mass %.

When the lipolysis stimulator or a similar agent is processed into an external preparation, the total amount of the Huang Hua Cai or the extract thereof and the xanthine derivative of the present invention is 0.005 mass % or more, preferably 0.01 to 30 mass %, more preferably 0.05 to 20 mass %, even more preferably 0.1 to 10 mass %.

When the lipolysis stimulator or a similar agent is processed into an oral preparation, the total amount of Huang Hua Cai or the extract thereof and the xanthine derivative of the present invention is generally 0.01 to 80 mass %, preferably 0.05 to 70 mass %, more preferably 0.1 to 50 mass %.

The ratio of the xanthine derivative content to the Huang Hua Cai (or the extract) content is at least 0.0001 parts by mass, preferably 0.001 to 10 parts by mass, with respect to 1 part by mass of a dried product of the Huang Hua Cai or the extract thereof.

When the lipolysis stimulator or a similar agent of the present invention is administered as a food product or a drug, the amount of administration, which varies depending on the forms of these effective ingredients and the administration route, may be selected from a wide range. From the viewpoint of the lipolysis-stimulating effect, the daily dose of Huang Hua Cai (as the plant Huang Hua Cai or the extract thereof) is 0.01 to 100 g for an adult, preferably 0.1 to 20 g, more preferably 1.0 to 10 g. The daily dose of the xanthine derivative is 0.001 to 10 g for an adult, preferably 0.01 to 5 g, more preferably 0.05 to 5 g.

The slimming method according to the present invention is carried out in order to slim a body down to look beautiful, and encompasses esthetic activities performed by a non-medical person such as an esthetician as well as medical activities performed by doctors or similar staff.

EXAMPLES

Preparation Example

Preparation of Huang Hua Cai Extract

A 50% (v/v) ethanol-water mixture (400 mL) was added to Huang Hua Cai (product of Shinwa Bussan) (40 g), and extraction was performed at room temperature (20 to 30° C.) for seven days. Subsequently, the extraction mixture was filtered, to thereby recover an extract (340 mL). Through evaporation of solvent under reduced pressure, 18.4 g of a dried product was yielded.

Test Example 1

The Huang Hua Cai extract produced in Preparation Example and commercially available caffeine (Wako Pure Chemical Industries, Ltd.) were employed.

The Rodbell's method (Rodbell, M., J. Biol. Chem., 239, 375 (1964)) was employed. Specifically, free adipocytes were recovered from the abdominal subcutaneous adipose tissue of each of one to three male Wistar rats (each having a body weight of 170 to 230 g) by use of a collagenase solution.

The following substances were tested: the Huang Hua Cai extract (singly), caffeine (singly), and two different mixtures of Huang Hua Cai extract and caffeine (hereinafter referred to as "Huang Hua Cai-caffeine mixture"), i.e., Huang Hua Cai-caffeine mixture 1 (Huang Hua Cai extract+10 μg/mL caffeine), and Huang Hua Cai-caffeine mixture 2 (Huang Hua Cai extract+30 μg/mL caffeine).

The free adipocytes were incubated at 37° C. for 2 hours in a Hanks buffer solution containing bovine serum albumin and 90 nM norepinephrine (reaction mixture) to which each test substance had been added. The resultant free glycerol was assayed through an enzymatic method (Free Glycerol Reagent, product of Sigma-Aldrich).

To the reaction mixture, added the Huang Hua Cai extract at the final concentration of 0, 3, 10, 30 and 100 μg/mL, respectively, and caffeine at the final concentration of 0, 10 and 30 μg/mL, respectively.

As a control, adipocytes were incubated in the same buffer containing only norepinephrine but no test substance.

Lipolysis-stimulating activity was calculated by the following equation, with 100% being a control value. The results are shown in Table 1 and FIG. 1.

Lipolysis-stimulating activity(%)=100×(free glycerol in each group)/(free glycerol in control group)

TABLE 1

| Caffeine | | Huang Hua Cai extract | | Huang Hua Cai-caffeine mixture 1 | Huang Hua Cai-caffeine mixture 2 |
|---|---|---|---|---|---|
| Concentration (μg/mL) | Activity (%) | concentration (μg/mL) | Huang Hua Cai extract | | |
| 3 | — | 3 | 112.9%* (1)** | 197.9% (1.75) | 304.8% (2.70) |
| 10 | 157.4% | 10 | 146.4% (1) | 217.2% (1.48) | 367.9% (2.51) |
| 30 | 207.1% | 30 | 177.3% (1) | 281.6% (1.59) | 397.5% (2.24) |
| 100 | — | 100 | 224.9% (1) | 328.0% (1.46) | 425.9% (1.89) |

*Activity (%) with respect to a control lipolysis-stimulating activity as 100%.
**Relative activity of Huang Hua Cai-caffeine mixture 1 or 2, with respect to lipolysis-stimulating activity (%) of Huang Hua Cai extract of each concentration as 1.
***Each concentration of Huang Hua Cai extract; Huang Hua Cai-caffeine mixture 1 (Huang Hua Cai extract of each concentration + 10 μg/mL caffeine); and Huang Hua Cai-caffeine mixture 2 (Huang Hua Cai extract of each concentration + 30 μg/mL caffeine).

As is clear from Table 1 and FIG. 1, caffeine, the Huang Hua Cai extract, and Huang Hua Cai-caffeine mixtures exhibited lipolysis activities higher than 100%. Among them, Huang Hua Cai-caffeine mixtures (combination of caffeine and Huang Hua Cai extract) exhibited particularly high lipolysis activity by virtue of synergism. When the caffeine content of each Huang Hua Cai-caffeine mixture increased, lipolysis was more stimulated.

Test Example 2

The procedure of Test Example 1 was repeated, except that caffeine was changed to theophylline. The following substances were tested: the Huang Hua Cai extract (singly), theophylline (singly), and two different mixtures of Huang Hua Cai extract and theophylline (hereinafter referred to as "Huang Hua Cai-theophylline mixture"), i.e., Huang Hua Cai-theophylline mixture 1 (Huang Hua Cai extract+1 μg/mL theophylline), and a Huang Hua Cai-theophylline mixture 2 (Huang Hua Cai extract+3 μg/mL theophylline).

Theophylline employed in the test was a commercial product (Sigma-Aldrich).

To the reaction mixture, added the Huang Hua Cai extract at the final concentration of 0, 10, 30 and 100 μg/mL, respectively, and theophylline at the final concentration of 0, 1 and 3 μg/mL, respectively.

Figure 2:
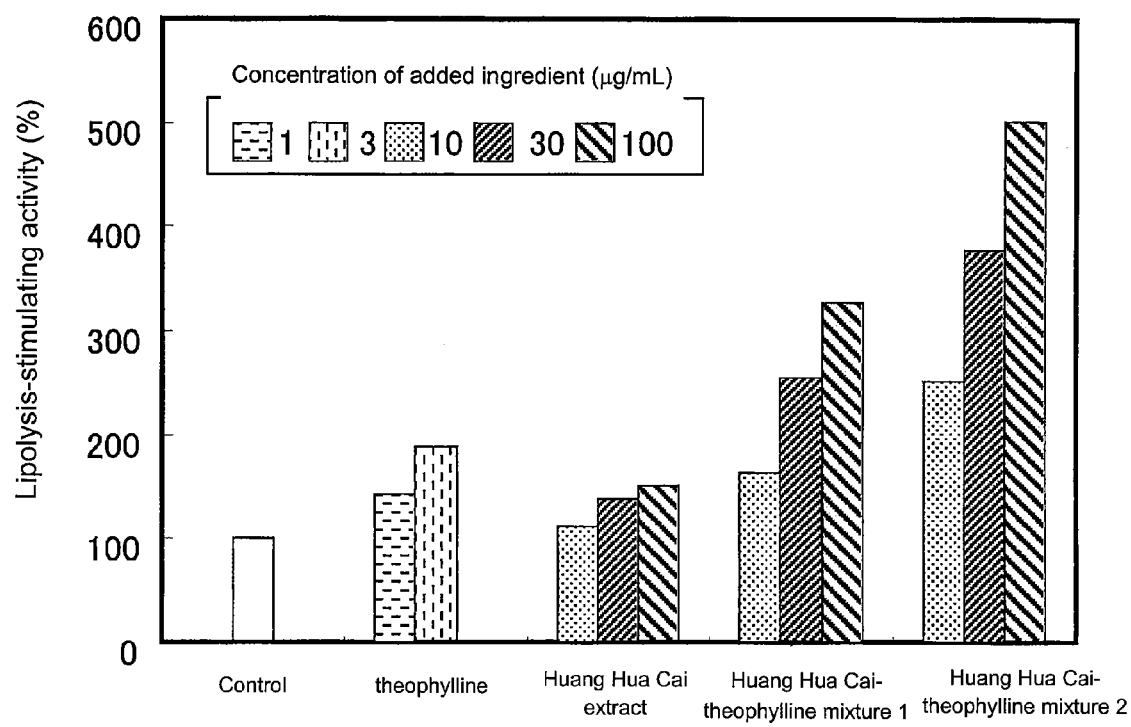

As is clear from Table 2 and FIG. 2, theophylline, the Huang Hua Cai extract, and Huang Hua Cai-theophylline mixtures exhibited lipolysis activities higher than 100%. Among them, Huang Hua Cai-theophylline mixtures (combination of theophylline and Huang Hua Cai extract) exhibited particularly high lipolysis activity by virtue of synergism. When the theophylline content of each Huang Hua Cai-theophylline mixture increased, lipolysis was more stimulated.

Test Example 3

The procedure of Test Example 1 was repeated, except that caffeine was changed to aminophylline. The following substances were tested: and two different mixtures of Huang Hua Cai extract and aminophylline (hereinafter referred to as "Huang Hua Cai-aminophylline mixture"), i.e., Huang Hua Cai-aminophylline mixture 1 (Huang Hua Cai extract+1 μg/mL aminophylline), and a Huang Hua Cai-aminophylline mixture 2 (Huang Hua Cai extract+3 μg/mL aminophylline).

Aminophylline employed in the test was a commercial product (Sigma-Aldrich).

To the reaction mixture, added the Huang Hua Cai extract at the final concentration of 0, 10, 30 and 100 μg/mL, respectively, and aminophylline at the final concentration of 0, 1 and 3 μg/mL, respectively.

TABLE 2

| Theophylline | | Huang Hua Cai extract | | Huang Hua Cai-theophylline mixture 1 | Huang Hua Cai-theophylline mixture 2 |
|---|---|---|---|---|---|
| Concentration (μg/mL) | Activity (%) | concentration (μg/mL) | Huang Hua Cai extract | | |
| 1 | 141.9% | 10 | 111%* (1)** | 164.0% (1.48) | 252.3% (2.27) |
| 3 | 188.3% | 30 | 137.5% (1) | 254.5% (1.85) | 378.1% (2.75) |
| — | — | 100 | 150.8% (1) | 327.3% (2.17) | 501.6% (3.33) |

*Activity (%) with respect to a control lipolysis-stimulating activity as 100%.
**Relative activity of Huang Hua Cai-theophylline mixture 1 or 2, with respect to lipolysis-stimulating activity (%) of Huang Hua Cai extract of each concentration as 1.
***Each concentration of Huang Hua Cai extract; Huang Hua Cai-theophylline mixture 1 (Huang Hua Cai extract of each concentration + 1 μg/mL theophylline); and Huang Hua Cai-theophylline mixture 2 (Huang Hua Cai extract of each concentration + 3 μg/mL theophylline).

TABLE 3

| | | Huang Hua Cai extract-aminophylline mixture*** | | | |
|---|---|---|---|---|---|
| Aminophylline | | Huang Hua Cai extract | | Huang Hua Cai- | Huang Hua Cai- |
| Concentration (μg/mL) | Activity (%) | concentration (μg/mL) | Huang Hua Cai extract | aminophylline mixture 1 | aminophylline mixture 2 |
| 1 | 140.5% | 10 | 111%* (1)** | 150.6% (1.36) | 245.7% (2.21) |
| 3 | 197.1% | 30 | 137.5% (1) | 170.8% (1.24) | 278.0% (2.02) |
| — | — | 100 | 150.8% (1) | 273.3% (2.17) | 411.6% (2.73) |

*Activity (%) with respect to a control lipolysis-stimulating activity as 100%.
**Relative activity of Huang Hua Cai-aminophylline mixture 1 or 2, with lipolysis-stimulating activity (%) of Huang Hua Cai extract of each concentration as 1.
***Each concentration of Huang Hua Cai extract; Huang Hua Cai-aminophylline mixture 1 (Huang Hua Cai extract of each concentration + 1 μg/mL aminophyl line); and Huang Hua Cai-aminophylline mixture 2 (Huang Hua Cai extract of each concentration + 3 μg/mL aminophyl line).

Figure 3:
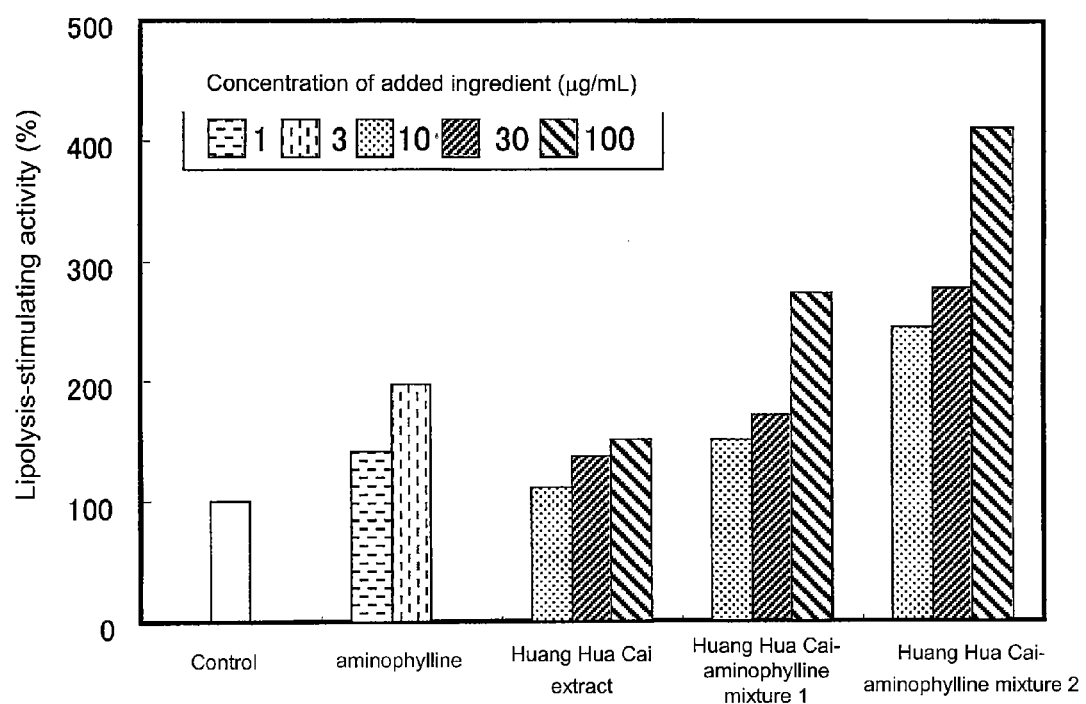

As is clear from Table 3 and FIG. 3, aminophylline, the Huang Hua Cai extract, and Huang Hua Cai-aminophylline mixtures exhibited lipolysis activities higher than 100%. Among them, Huang Hua Cai-aminophylline mixtures (combination of aminophylline and Huang Hua Cai extract) exhibited particularly high lipolysis activity by virtue of synergism. When the aminophylline content of each Huang Hua Cai-aminophylline mixture increased, lipolysis was more stimulated.

The invention claimed is:

1. A lipolysis stimulator that has body-slimming and cellulite-reducing effect, comprising a plant Huang Hua Cai or an extract thereof, at a concentration of at least 3 μg/ml and caffeine at a concentration of at least 10 μg/ml.

2. A lipolysis stimulator that has body-slimming and cellulite-reducing effect, comprising a plant Huang Hua Cai or an extract thereof, at a concentration of at least 10 μg/ml and theophylline at a concentration of at least 1 μg/ml.

3. A lipolysis stimulator that has body-slimming and cellulite-reducing effect, comprising a plant Huang Hua Cai or an extract thereof, at a concentration of at least 10 μg/ml and aminophylline at a concentration of at least 3 μg/ml.

4. The lipolysis stimulator of claim 1, wherein the concentration of the plant Huang Hua Cai or an extract thereof is at least 10 μg/ml.

5. The lipolysis stimulator of claim 2, wherein the concentration of the theophylline is at least 3 μg/ml.

6. A method of stimulating lipolysis that has body-slimming and cellulite-reducing effect, comprising administering a plant Huang Hua Cai or an extract thereof, at a concentration of at least 3 μg/ml and caffeine at a concentration of at least 10 μg/ml to a subject in need thereof.

7. A body-slimming method, comprising applying a plant Huang Hua Cai or an extract thereof, at a concentration of at least 3 μg/ml and caffeine at a concentration of at least 10 μg/ml to the skin of a subject in need thereof.

* * * * *